(12) United States Patent
Benes et al.

(10) Patent No.: US 9,005,574 B2
(45) Date of Patent: *Apr. 14, 2015

(54) PROTEINS WITH HIGH IMMUNOREACTIVITY AND METHOD FOR THEIR PRODUCTION

(75) Inventors: Ivan Benes, Forch (CH); Silke Thomsen-Bosslet, Berlin (DE)

(73) Assignee: Scintec Diagnostics, Zug (CH)

( * ) Notice: Subject to any disclaimer, the term of this patent is extended or adjusted under 35 U.S.C. 154(b) by 165 days.

This patent is subject to a terminal disclaimer.

(21) Appl. No.: 12/883,620

(22) Filed: Sep. 16, 2010

(65) Prior Publication Data

US 2011/0008249 A1    Jan. 13, 2011

Related U.S. Application Data

(60) Division of application No. 11/888,483, filed on Aug. 1, 2007, now Pat. No. 7,820,410, which is a continuation of application No. 10/240,912, filed as application No. PCT/EP01/03867 on Apr. 4, 2001, now Pat. No. 7,264,805.

(30) Foreign Application Priority Data

Apr. 5, 2000    (DE) .................. 100 16 877

(51) Int. Cl.
| | |
|---|---|
| *A61K 51/10* | (2006.01) |
| *C07K 16/28* | (2006.01) |
| *C07K 16/00* | (2006.01) |
| *A61K 39/00* | (2006.01) |

(52) U.S. Cl.
CPC ........... *A61K 51/10* (2013.01); *A61K 2039/505* (2013.01); *C07K 16/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,873,316 A | | 10/1989 | Meade et al. |
| 4,939,087 A | | 7/1990 | Van Wie et al. |
| 5,132,405 A | | 7/1992 | Huston et al. |
| 5,541,294 A | | 7/1996 | Horowitz et al. |
| 5,645,817 A | * | 7/1997 | Seemann et al. ........... 424/9.341 |
| 5,648,472 A | | 7/1997 | Gehringer et al. |
| 5,723,102 A | * | 3/1998 | Bremer et al. .............. 424/1.69 |
| 6,241,961 B1 | | 6/2001 | Benes et al. |
| 7,264,805 B2 | | 9/2007 | Benes et al. |

FOREIGN PATENT DOCUMENTS

| | | |
|---|---|---|
| DE | 38 52 255 T2 | 5/1995 |
| DE | 196 21 388 A1 | 12/1996 |
| DE | 197 44 531.4 | 10/1997 |
| EP | 0 727 480 A2 | 8/1996 |
| EP | 0 585 570 | 11/1998 |
| WO | WO 86/05202 | 9/1986 |
| WO | WO 96/22310 | 7/1996 |

OTHER PUBLICATIONS

Piatesi et al, ChemBio Chem 5: 460-466, 2004.*
MacCallum et al, J. Mol. Biol 262: 732-745, 1996.*
Pascalis et al, The Journal of Immunology 169: 3076-3084, 2002.*
Chen et al, J. Mol. Bio. 293: 865-881, 1999.*
Wu et al, J. Mol. Biol. 294: 151-162, 1999.*
Bruynck et al, Br J Cancer 67: 436-440, 1993.*
Harlow et al., in Antibodies a Laboratory Manual, 1998, Cold Spring harbor laboratory publication, Cold Spring Harbor, NY, pp. 285-311.*
Cochran et al., J. Immunol. Meth. 287: 147-158, 2004.*
Riemer et al., Mol. Immunol. 42: 1121-1124, 2005.*
A. Bruynck et al: Characterisation of a humanised bispecific monoclonal antibody for cancer therapy, in: Br. J. Cancer, pp. 436-440, 1993.
Dux et al.: "Determination of immunoreactive fraction and kinetic parameters of a radiolabeled monoclonal antibody in the absence of antigen excess", in: Journal of Immunological Methods, pp. 175-183, 1991.
Seccamani et al.: "Standardization of an immunoreactivity test for radiolabelled monoclonal antibodies", in: Nuklearmedizin Supplement, pp. 709-711, 1989.
Guo Xuegang et al.: "A method to determine the affinity constant of an antibody and antigen density on cell surfaces", in: Science Press, 1993.
Rucoff et al. in: Proc. Natl Acad of Science USA, vol. 79, pp. 1979-1983, 1982.
Barrios et al. in: J. Molecular recognition, vol. 17, pp. 332-338, 2004.
Lindmo et al.: "Determination of the immu oreactive fraction of radiolabeled monoclonal antibodies . . . ", in: Journal of Immun. Methods, pp. 77-89, 1984.
Seitz et al.: "Preparation and evaluation of the rhenium-188-labeled anti-NCA antigen monoclonal antibody . . . ", in: Europ. Jour. of Nuc. Med., Oct. 10, 1999.
Jagoda et al.: "An affinity column method for determination of the immunoreactivity of . . . ", in: Journ. of Immun. Meth., Nov. 12, 1993.
Mattes: "Limitations of the Lindmo method in determining antibody immunoreactivity", in: In. Int. J. Cancer, pp. 286-288, 1995.

(Continued)

*Primary Examiner* — Phuong Huynh
(74) *Attorney, Agent, or Firm* — Ursula B. Day; Law firm of Ursula B. Day

(57) ABSTRACT

The invention relates to (glyco-) proteins, in particular monoclonal antibodies, which have an immunoreactivity of >81%, preferably >90%. The inventive monoclonal antibodies are produced using a fluidized bed reactor in conjunction with a conventional protein-chemical purification method or preferably with a purification method involving less column chromatography. The monoclonal antibodies thus produced are suitable, in gamma-irradiated form, e.g. Tc-99m labeled, for the in vivo diagnosis of inflammatory diseases and bone marrow metastases. In alpha- or beta-irradiated form, e.g. astatine or Re-188 or Y-90 labeled form, the inventive monoclonal antibodies can be used, for example, in the treatment of leukemia.

8 Claims, 9 Drawing Sheets

(56) References Cited

OTHER PUBLICATIONS

Morales-Morales et al.: "Biodistribution of 99m-Tc-labaled anti-human epidermal growth factor . . . ", in: Nucl. Med. & Biol., vol. 26, pp. 275-279, 1999.
Boven et al.: "Selective cytotoxicity of 125-I-labeled monoclonal antibody T101 in human malignant . . . ", in: Blood, vol. 67, No. 2, 1986, pp. 429-435.
Schubinger et al.: "Assessment of the binding properties of granuloszint", in: Eur. Journ. of Nucl. Med., vol. 15, 1989, pp. 605-608.
Bosslet et al.: "Quantitative cosiderations sporting the irrelevance of circulating serum CEA . . . ", in: Eur. J. of Nucl. Med., vol. 14, 1988.
Bosslet et al.: "Immunohistochemical localization and molecular characteristics of three . . . ", in: J. Cancer, vol. 36, 1985, pp. 75-84.
Bosslet et al.: "Molecular and functional characterisation of a fusion protein suited . . . ", in: Br. J. Cancer, vol. 65, 1992, pp. 234-238.
Alles et al.:"Immunohistochennical and Immunochemical characterization . . . ", in: Jour. of Histochemistry and Cytochemistry, vol. 34, No. 2, 1986.
Hale et al.: "Therapeutic potential of rat monoclonal antibodies:isotype specificity of . . . ", in: Jou. of Immunology, vol. 134, No. 5, May 1985.
Cobbold et al.: "Non-lineage, LFA-1 family and leucocyte common antigens: new and . . . ", in: Oxford, pp. 788-803, approx. 1988.
Berthold et al.: "Detection of minial disease in bone marrow of neuroblastoma patients . . . ", in: Pediatric Hemat. & Oncol., vol. 6, 1989, pp. 73-83.
Schwarz et al.: "A novel approach to Tc-99m-labeled monoclonal antibodies", in: Jour. f. Nucl. Med., vol. 28, No. 4, Apr. 1987, p. 721.
R. Weibel et al.: "Stable one-step technetium-99m labeling of His-tagged recombinant proteins with a novel Tc(I)-carbonyl complex", Nature Biotechnology, Sep. 1999, vol. 17, XP-002156715, pp. 897-901.
Kuby et al., 1994, Immunology, second edition, pp. 85-96.
Stryer et al, in Biochemistry, Third edition,W H Freeman Company, New York, pp. 31-33, 1998.
Jantscheff et al., J Leukocyte Biology 59: 891-901, Jun. 1996.
Bunjes et al., Blood 98(3): 565-572, Aug. 2001.
Harlow et al, n Antibodies a Laboratory Manual, 1998, Cold Spring harbor laboratory publication, Cold. Spring Harbor, NY, pp. 285-311.
Troccoli et al, Biologicals 26: 321-329, 1998.
Bunjes: Re-labeled anti-DC66 monoclonal antibody in stem cell transplantation for patients with high-risk acute myeloid leukemia:, in: Leukemia & Lymphoma, vol. 43, 2002, pp. 2125-2131.
Buchmann et al.: "Radioimmunotherapy for treatment of acute myeloid leukaemia and myolddysplastic syndrome", in: Nuklearmedizin, No. 3, 2005, pp. 107-117.
Steve Cobbold et al.: "Non-lineage, LFA-1 family and leucocyte common antigens: new and previously defined clusters", in: Leucocyte Typing III, Oxford University Press, 1988.
Maik Hirschhäuser: "Zur Differenzierung von Endothel und Syncytium (Endotheläquivalet) im Bauplan der menschlichen Placenta haemochorialis. Eien lichtmikroskopische Studie", Inaugural Disertation, Giessen, 2006.
Y.R. Mahida et al.: Monoclonal antigranulocyte antibody imaging in inflammatory bowel disease: a preliminary report:, in: Nuclear Medicine Communications No. 13, 1992, pp. 330-335.
Fritz Scheikart et al.: "Rapid structural characterization of a murine monoclonal IgA α chain: heterogeneity in the . . . ", in: Journal of Biotechnology No. 69, 1999, pp. 191-201.
T. Fabre et al.: "Quantification of the inflammatory response in exudates to three polymers implanted in vivo", in: Journal of Biomedical Materials Research, vol. 39, 1998, pp. 637-641.
Jens j. van der Pol et al.: On-line monitoring of an animal cell culture with multi-channel flow injection analysis:, in: Journal of Biotechnology No. 37, 1994, pp. 253-264.
Marie-Helene Ruchaud-Sparagano et al.: "Activation of neutrophil function via CD66: differential effects upon $\beta_2$ integrin mediated adhesion", in: British Journal of Haematology, No. 98, 1997, pp. 612-620.
Jan W. Gratama et al.: Analysis of Variation inf Results if CD34+ Hematopoietic Progenitor Cell Enumeration in a Multicenter Study, in: Cytometry No. 30, 1997, pp. 109-117.
Graziella Mazza et al.: "The separation and identification by monoclonal antibodies of dog IgG, fractions", in: Journal of Immunological Methods No. 161, 1993, pp. 193-203.
Mark R. Wicke et al.: "Epithelioid sarcoma and epithelioid hemangioendothelioma: an immunocytochemical and lectin-histochemical comparison", in: Virchows Archly A No. 410, 1987, pp. 309-316.
P. Clezardin et al.: "Tandem purification of mouse IgM monoclonal antibodies produced in vitro using anion-exchange and gel fast protein liquid chromatography", in: Journal of Chromatography No. 358, 1986, pp. 209-218.
Gianfranco Gennarini et al.: "Studies on the transmembrane disposition of the neural cell adhesion molecule N-CAM", in: European Journal of Biochemistry No. 142, 1984, pp. 57-64.
P. Benz et al.: "Monoclonal antibody BW431/26 labelled with technetium99m and indium 111: an investigation . . . ", in: European Journal of Nuclear Medicine vol. 18, No. 10, 1991, pp. 813-816.
Robert C. Dean et al.: "Large-Scale Culture of Hybridoma and Mammalian Cells in Fluidized Bed Bioreactors", in: Annals New York Academy of Sciences, vol. 506, 1987, pp. 129-146.
N.G. Ray et al.: "Continuous Cell Cultures in Fluidized-Bed Bioreactors", in: Annals New York Academy of Sciences, vol. 589, 1990, pp. 443-457.
Murayama et al.: "Monoclonal Antibody Production Using a Large Scale Animal Cell Culture Technique", in: Forschungsbericht K K Toso, vol. 38, 1994, pp. 79-87.

* cited by examiner

RT    ANT    LT

LT    POST    RT

PROTEINS WITH HIGH IMMUNOREACTIVITY AND METHOD FOR THEIR PRODUCTION

CROSS-REFERENCES TO RELATED APPLICATIONS

This application is a divisional of prior filed copending application application Ser. No. 11/888,483 which is a continuation of prior filed application application Ser. No. 10/240,912, filed Oct. 4, 2002 now U.S. Pat. No. 7,264,805, which is the national phase of copending PCT International application No. PCT/EP01/03867, filed Apr. 4, 2001 and which claims the priority of German Patent Application Serial No. 100 16 877.9, filed Apr. 5, 2000, pursuant to 35 U.S.C. 119(a)-(d), the subject matter of which is incorporated herein by reference.

BACKGROUND OF THE INVENTION

The invention relates to preparations of immunoreactive proteins and in particular in purified form and having a high percentage of immunoreactive molecules relative to the total number of molecules. These proteins can be obtained through fermentation in a fluidized reactor of a host cell, which is capable of expressing the immunoreactive protein and production of the protein from the host cell respectively from the culture medium used for culturing the cells. The protein preparations according to the invention are outstandingly suitable for producing diagnostic and therapeutic compositions.

Diagnostic and therapeutic proteins can be expressed in prokaryotic cells, such as for example *E. coli* (Houston et al., U.S. Pat. No. 5,132,405) as well as in eukaryotic cell systems, (for example *Pichia pastoris*, baby hamster kidney (BHK) cells, Chinese hamster Ovary (CHO-)cells, hybridomas, transgenic animals and plants (Meade et. al., U.S. Pat. No. 4,873,316) and can be purified by protein-chemical methods.

With prokaryotic cell systems, a cost efficient production of small carbohydrate-free proteins can be realized due to the simple culture media and the fast growth of the microorganisms in relatively simple fermentation systems.

However, for the production of complex, carbohydrate-carrying (glyco-) proteins, the afore-described eukaryotic cells systems have to be used which require complex fermentation systems and require the use of expensive culture media. The compositions of the glyco-protein preparation that are to be purified are being decisively influenced by the type of culture medium and the fermentation system used. In particular, differences of the glycosylation of the protein, which influences the half-life in the plasma as well as certain biological effector functions of the purified (glyco-) protein preparation are described in the respective technical literature. (Stahl et al., PNAS, 73 (1976), 4045-4049).

In addition to the afore-described influences on the carbohydrate composition, an essential factor which determines the quality of the product is the percentage share of functionally active (glyco-) proteins in the purified preparation, which can be also influenced by the type of cell media used, the conditions of fermentation and the purification methods applied.

As a preferred method used for determining the portion of functionally active radio-labeled molecules (for example Mab with physiological intact V-region) is the quantitative binding assay first described by Lindmo et al. (Immunological Methods 72 (1984) 77) in which an excess of antigen was used. This methods permits a quantitative determination of the immunoreactive and radioactive labeled Mab (monoclonal antibody) portion having a bonding capacity, after protein chemical purification. Other binding assays, such as the immunoreactivity test of Seitz et al. (European Journal of Nuclear Medicine 26 (1999), 1265) where immunoreactivities of up to 100% are described, permit only a relative determination of the immunoreactive portion of radio-labeled Mab in comparison to the unlabelled standard and are thus not suitable for determination of the absolute immunoreactive fraction. Similarly, the method described by Jagoda et al. (Journal of Immunological Methods 173 (1994), 191-201) directed to an affinity-chromatographic method for determining immunoreactivity has only limited applicability for a quantitative determination of the immunoreactive portion due to the relatively high portion of unspecific linkage with the affinity column (10-20%).

Likewise, the Lindmo-test utilized by most authors, and despite the authors claim that the method has general applicability, it is only suitable for the evaluation of radio-labeled Mab where binding can be realized to a distinct plateau by utilizing increasing amounts of antigen. Oftentimes, a distinct plateau is not reached with Mabs of low avidity or with a lack of cells that express high antigen densities per cell (Mattes, M. J., Int. J. Cancer: 61 (1995), 286-288) Even in investigations, where a definitive plateau can be reached, plotting the data from the saturation curves according to the Lindmo et al. method, produces two straight crossed lines, where the intersection with the Y-axis can lead to differing immunoreactivities. (Mattes, M. J., Int. J. Cancer: 61 (1995), 286-288, page 287, FIGS. 1B and E). Thus, when using the Lindmo method the maximal specifically linked radioactive portion and the value extrapolated to the infinite antigen excess must be given. When the difference between these two values is >10%, then the extrapolated immunoreactivity value cannot be regarded as reliable (Mattes M. J., Int. J. Cancer: 61 (19915), 286-288, page 288).

With regard to the afore-described reservations concerning that method, when using the Lindmo test, the percent portion of the functionally active Mab molecule prepared with conventional fermenting methods, such as for example stirred fermentors and hollow fiber modules and purified with classical protein chemical methods which also comprise, besides protein A-columns, ion exchanger columns and in many cases also gel-chromatographic columns, is in the range of 40-80% (Mattes, M. J., Int. J. Cancer: 61 (1995), 286-288; Jagoda et al., Journal of Immunological Methods 173 (1994), 191-201; Morales-Morales et al., Nuclear Medicine & Biology, Vol. 26 (1999), 275-279; Boven et al., Blood, 67, N9 2 (1986), 429-435). Here, the radio-labeling method and the radioisotope used likewise have an important role.

This means that 20-60% of the Mab molecules of these prepared preparations do not carry out the desired diagnostic or therapeutic function due to their production method.

One exception known in the literature is the granulascint described by Schubinger et al., (Eur. J. Nucl. Med. 15: (1989), 605-608) where an immunoreactivity of 93 respectively 40% is described, depending on the respective labeling methods. However, this Mab was produced in the form of ascites (personal communication). This in vivo method fulfills neither economic nor modern regulatory requirements and therefor has to be regarded as an exception. Furthermore, it is noted, that the portion of the really specifically binding Mab molecules is smaller than the value determined in the Lindmo test. This is the result of the unspecific binding of radio-labeled Mab to e. g. the granulocytes used in an antigen excess even with the addition of a 10 000 times molar excess of unlabelled Mab (Schubinger et al., Euro J. Nucl. Med., 15 (1989), 605-

608). Accordingly, after subtraction of unspecific binding the immunoreactivity value is at <90%.

In the case of radio-labeled diagnostic monoclonal antibodies, a reduced immunoreactivity of the Mab is a definite disadvantage, since radio-labeled molecules that are not binding to the specific target structure circulate in the blood, contribute to the unspecific background are partially absorbed by the liver and Mab the interpretation of nuclear-medical diagnosis more difficult. In the case of radio-labeled therapeutic antibodies, the portion of the Mab molecules not bound to the target tissue contributes to the unspecific and undesired irradiation of non-target tissue.

It is thus of great importance in particular for producing radio-labeled monoclonal antibodies to provide economically efficient in vitro methods that pass regulatory acceptance and with which production of Mab preparations that have an as high as possible immunoreactive portion can be realized.

At this time, highly immunoreactive portions can only be realized by means of complex immunoaffinity-chromatographic methods which are not suitable for subsequent commercialization by the pharma industry. Here, the functionally active molecules are separated from the functionally inactive molecules which are protein-chemically not distinguishable from the active molecules, through binding to antigen columns whereby they are also concentrated. Despite the relatively high cost in the production of the reagents necessary for the immunoaffinity chromatography and the high losses during purification, the portion of the functionally active Mab in such preparations utilized for research purposes is even <81%.

SUMMARY OF THE INVENTION

In order to be able to measure with certainty the immunoreactive portion of the non-labeled Mab as well as the labeled Mab, a "modified Lindmo test" was developed, which is described infra in detail in Example 3. In this modified Lindmo test the portion of unspecifically binding Mab-molecules (as for example found after radio labeling with a 10 000-fold excess of cold Mab, Schubinger et al. Euro J. Nucl. Med., 15 (1989), 605-608) does not influence the computed immunoreactivity value.

Within the scope of researching an optimization of the production methods for the monoclonal antibody, BW 250/183 (Eur J. Nucl. Med. 14 (1988), 523-528 and Int. J. Cancer 36 (1985), 75-84) it was surprisingly possible to develop a fermentation method which produces cell culture supernatants which contain Mab with an immunoreactivity as shown by the modified Lindmo Test to be regularly >95%.

From these cell culture supernatants, Mab preparations can be produced by using conventional purification methods (also corresponding to GMP), and which exhibit an immunoreactivity between 80 and 90%. The loss in immunoreactivity observed here of about 10% during the purification is due to the multiple steps of column chromatography.

Furthermore, a "column-reduced" purification method was developed, with which Mab preparations can be produced (also GMP corresponding) that shows an immunoreactivity in the modified Lindmo test, which does not significantly differ from that of the non-purified Mab molecules found in the cell culture supernatant (loss of about 1-2%).

These methods can be applied to a variety of Mabs of differing specificities and protein chemical compositions as well as to other immunoreactive proteins, and they produce also in these cases comparably surprising results.

The invention relates to a preparation of immunoreactive proteins, wherein the per cent portion of the immunoreactive molecules, determined by a modified Lindmo test is >81%, preferably >90% and most preferred >95% relative to the entire number of molecules. The immunoreactive proteins can be obtained by production in cell culture, in particular in eukaryotic host cells. The immunoreactive proteins can be coupled to markers, in particular a radioactive marker, without any loss of reactivity.

Immunoreactive proteins according to the invention are proteins that have at least one antibody-binding domain. Examples for such proteins are antibodies, in particular monoclonal antibodies, chimerical antibodies, humanized antibodies, recombinant antibodies such as single chain antibodies or fragments thereof, e.g. proteolytic fragments, such as Fab-, Fab'-or F(ab)$_2$-fragments or recombinant antibody fragments, such as single chain Fv-fragments.

In addition to antibodies and antibody fragments, fusion proteins can likewise be utilized, which comprise at least one antibody binding domain and a further binding domain, for example an effector domain, such as an enzyme or a cytokine. Examples thereof are scFv-Cytokine, e. g. scFv-IL1, scFv-IL2, scFv-IL6, scFv-IL10, scFv-IL11, scFv-IL12, scFv-TNF, scFv-IFNγ, scFv-IFNβ, scFv-IFNα, or scFv-coagulation agents, such as for example scFv-tTF, scFv-(Deoxy) ribonucleases or fusion with enzymes, such as the fusion protein described in British J. Cancer 654 (1992), 234-238 which comprises the heavy chain VH-CH1 of the humanized Mab BW 431/26 fused via hingelinker to β-glucuronidase and the humanized VL-CL light chain of the same humanized Mab.

The protein preparations in accordance with the invention are obtainable through fermentation in a fluidized bed. In such a fluidized bed, the cultured host cells, for example hybridoma—or other eukaryotic cells are grown in high density on glass spheres and can be optimally provided with oxygen and nutrients. Dying cells detach from the glass spheres and are continuously removed together with the harvested medium from the fermentation system. Thus, the amounts of proteases and cell debris can be kept to a minimum in the fermentation system whereby the integrity of the produced protein is realized. One example of a suitable fluidized-fermentation reactor is bioreactor Pilot B 500 (Papaspyrou Biotechnologie GmbH).

Measurement of the immunoreactivity of the protein preparations according to the invention is carried out by means of the modified Lindmo test described in Example 3. When carrying out this test, it is essential that an excess amount of the antigen containing material is used in order to quantitatively bind the immunoreactive protein, e. g. the Mab. Furthermore, it is important; that the antigen containing material contains a sufficient amount of epitopes, so that unspecific adsorption effects caused by large surfaces can be disregarded. Thus, epitope densities of >10$^4$ per fixed cell are preferred. The immunoreactivity is read at the point at which the control Mab (same isotype as the test Mab, but having non-relevant binding region) does not show a significant unspecific adsorption.

The following describes in addition to the fermentation method according to the invention and the "column-reduced" purification method, also the protein preparations according to the invention that result therefrom and their advantageous use as diagnostic and therapeutic tools.

The two methods in accordance with the invention I and II are comprised in each case of two sections, which can be further subdivided into several single steps.

| Production Method I (general) | Production Method II (general) |
|---|---|
| Culturing of eukaryotic cells and their fermentation in a fluidized reactor | Culturing of eukaryotic cells and their fermentation in a fluidized reactor |
| Proteinchemical purification with a conventional purification system | Proteinchemical purification with a "column reduced" purification method |

Production Method I (Specific):

Culturing of Eukaryotic Cells and their Fermentation, in a Fluidized Reactor:
1. defrosting cells from the cell bank and culturing for example in T-flasks
2. expanding cells for example in Spinner cultures
3. fermentation in the fluidized reactor Protein-Chemical Purification with Conventional Purification Methods
1. harvesting the cell culture medium, separating cells e. g. by means of microfiltration, sterile filtration and storage, for example at −20° C.;
2. concentrating, for example by means of ammonium sulfate precipitation and subsequent centrifugation;
3. dissolution; deactivating of virus by means of detergent treatment and sterile filtration;
4. submitting to affinity-chromatography with protein A or similar affinity system;
5. concentrating for example by means of ammonium sulfate precipitation and subsequent centrifugation
6. dissolution, rebuffering by means of gel-chromatography
7. anion exchange chromatography
8. concentrating for example by means of ammonium sulfate precipitation and subsequent centrifugation;
9. dissolution, rebuffering by means of gel-chromatography;
10. adjusting the final desired concentration of the batch;
11. sterile filtration.

Production Method II (Specific)

Culturing Eukaryotic Cells and their Fermentation in a Fluidized Reactor
1. defrosting cells from the cell bank and cultivating cells, for example in T-flasks;
2. expanding cells, for example in spinner-cultures;
3. Fermentation in the fluidized reactor.

Protein-Chemical Purification with a "Column Reduced" Purification Method
1. harvesting of the cell culture medium, cell separation, for example by means of micro filtration, sterile filtration and storage, for example at −20° C.;
2. defrosting of the sterile and cell-free culture, harvest followed by microfiltration and ultrafiltration;
3. dilution;
4. treatment with detergent;
5. submitting to affinity-chromatography with protein A or similar affinity system;
6. dilution and sterile filtration;
7. anion exchange-membrane adsorption;
8. virus filtration by means of ultrafiltration;
9. ultrafiltration and diafiltration;
10. filtration and dilution;
11. sterile filtration.

The above shown individual production method steps are each known to the skilled artisan (cell biologists/protein chemists) and need not be further described. Notwithstanding that, the method is extensively described herein in Example 2.

Production method I is novel in that the fermentation is carried out with the fluidized reactor in combination with a conventional purification method.

Surprisingly, the immune reactivity of the Mab in unpurified cell culture supernatants (T-flasks, fluidized reactor) is >90% in the modified Lindmo test. In accordance with conventional purification, immunoreactivities of >80% are realized.

The novelty of production method II is the fermentation by means of a fluidized reactor in combination with the "column-reduced" purification method, wherein only one column purification chromatography (affinity chromatography at protein A) is utilized. All other steps are either gentle filtration steps by means of membranes or simple dilution steps. The method according to the present invention also fulfills the requirements of the respective governing approval agency concerning the protein chemical purity and the virus depletion and the inactivation.

Surprisingly, the immunoreactivity of the (glyco-) protein, for example an Mab, at all tested levels (T-Flasks, fluidized reactor, purified protein) is >90% in the Lindmo test, most often even 95% as shown in exemplary manner in Example 1 for the Mab BW 250/183. Comparatively high immunoreactivity values for in vitro production methods disclosed in the prior art have not been achieved.

Similarly high immunoreactivity values are found with the method according to the present invention for other Mabs, such as for example Mab BW 431.26 9 selective for CD 66e) (Eur. J. Nucl. Med. 14 (1988), 523-528 and Int. J. Cancer 36 (1985), 75-84), Mab BW 278/105 (selective for a subpopulation of FVIII RAG) (J. Histochem. Cytochem. 34 (1986), 209-214), Mab BW 575/931 (selective for N-CAM) (Pediatr. Hematol. Oncol. 6 (1989), 73-83) and Mab YTH 24.5 (selective for CD 45) (J. Immunol 134 (1985), 3056-3061 and Leucocyte Typing III: White Cell Differentiation Antigens (released McMichael et al.), Oxford University Press, Oxford, pp 788-803 and several Mabs described in the German patent application 197 44 531.4 (selective for the VEGF/VEGF-receptor complex, which however bind neither to the VEGF nor to the VEGF-receptor by itself). These findings show that with the production method according to the present invention, fermentation of (glyco-) proteins is realized, which are immune reactive to approximately 100% and which can be purified gently and rapidly, in the case of production method II without any traceable loss in immunoreactivity and in an economically efficient manner.

Furthermore, the production methods according to the present invention for the GMP-commensurate production of a multitude of (glyco-) proteins having no Fc-portions can be utilized, among others, for the fusion protein described by Bosslet et al. (British Journal of Cancer, 645 (1992), 234-238), wherein instead of the A-protein affinity chromatography, an alternative affinity chromatography procedure was utilized (anti-idiotype, lectin column, protein L, nickel acid etc.)

In addition to testing the immunoreactivity, a number of quality controls are conducted at the respective production levels such as for example tests for sterility, DNA content, protein content, specificity, pH value, protein composition, iso-electric point, pyrogenes, protein A-content in the end product), which permit testing the microbiological, immunological and proteinchemical properties of the produced (glyco-) protein (Mab) to be produced. As these tests are known in the prior art, they are not described here in detail.

Furthermore, the invention is explained by means of the following examples in connection with the drawings, in which:

DESCRIPTION OF PREFERRED EMBODIMENTS

Figure 1:
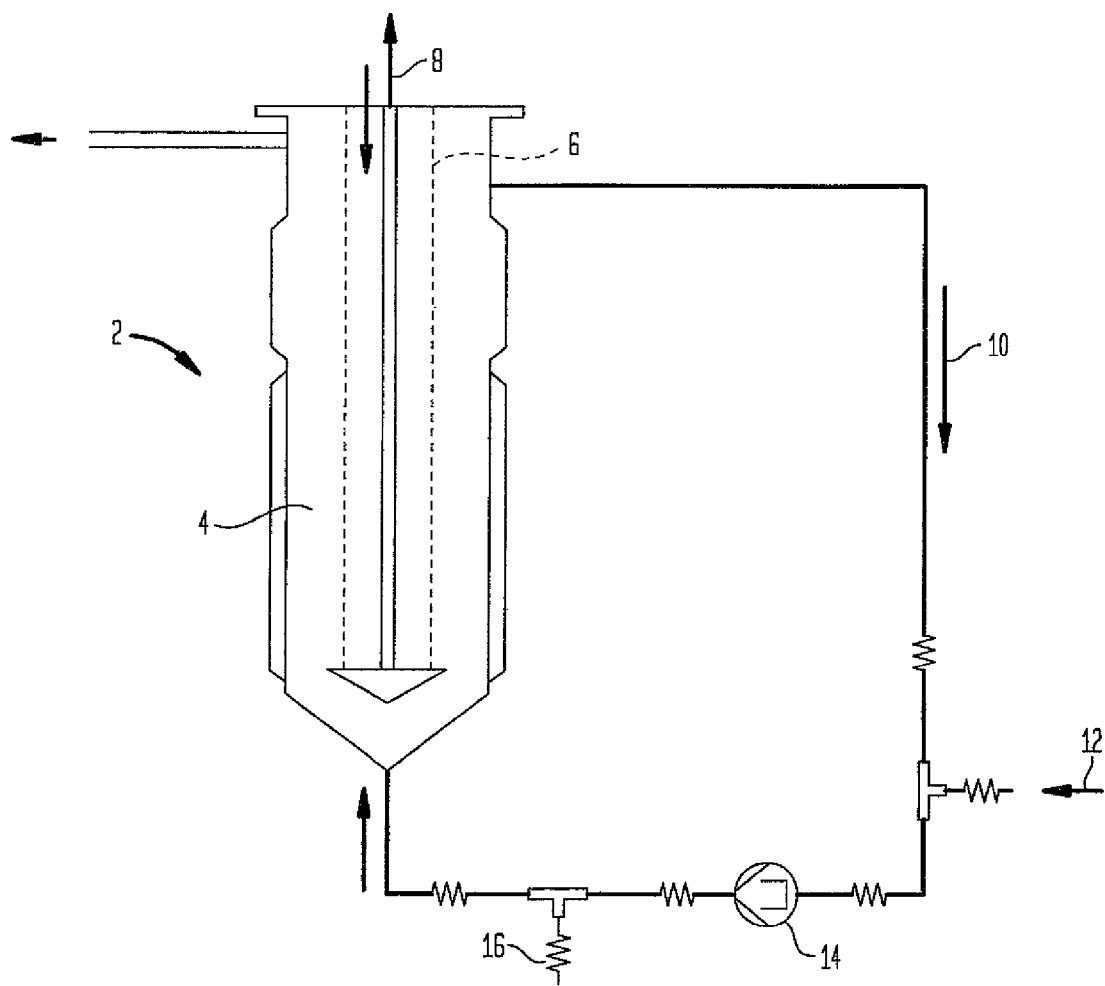
FIG. 1 is a schematic view of fluidized reactor.

The reactor 2 of FIG. 1 is partially filled with carrier spheres 4, for example glass spheres of open-pore sintered glass having a diameter of preferably about 0.4 to 0.7 mm, which have undergone an acid treatment (e.g. 2.5 N HCl and 5% nitric acid) and which, after neutralizing them are subjected to heat treatment for sterilization. (e.g. 220° C. for 6 hrs). Furthermore, the reactor is provided with an aeration module (6) for blowing a gas mixture (8), first into the reactor for whirling around the carrier spheres, and then released again to the outside. The reactor is furthermore provided with pH electrodes, oxygen electrodes temperature probes and similar. The medium is being recirculated in a circulation (10) with flow speed of for example 450 to 500 ml/min. The circulation can be provided with an inlet for the fresh medium (12), a pump (14) and a sample drawing valve (16). From line (18), medium is withdrawn for the harvest of the protein contained therein.

Following are the results of a typical immunoreactivity test for an Mab, as an example recited for Mab BW 250/183.

EXAMPLE 1

This example is directed to the comparison of the immunoreactivity of Mab BW 250/183 (Eur. J. Nucl. Med. 14 (1988), 523-528) measured with the modified Lindmo-test (see Example 3 for method) at conventional fermentation and purification and the two new fermentation and purification procedures (production method I and production method II) described herein each prior to starting the purification (cell supernatant) and after ending the purification (purified Mab-end product).

The Mab-containing samples of the cell supernatants respectively the purified Mab-end products were treated, as exactly described in Example 3, and then undergo the modified Lindmo-test according to the prescribed protocol. An Mab from the identical isotype ($IgG_1$) was used as a negative control having the same light chain ($\kappa$), a comparable isoelectric point and a non-relevant specificity. The positive control is a charge of a Mab BW 250/183 with an immunoreactivity of 91 to 94% purified with an antigen column in an analytic scale.

Following are the results of each of the immunoreactivity tests of the cell supernatants and the purified Mab end products.

1. Conventional Fermentation Method and Conventional Purification Method (Prior Art)
a) Non-Purified Cell Culture Supernatant (ZKÜ) according to Conventional Fermentation (KF)

TABLE 1

|  | Tested mass in ng | Starting mass in ng | Immuno reactivity |
|---|---|---|---|
| negative control | — | 50.0 | — |
| positive control | 3.2 | 48.0 | 93.3% |
| 250/183, ZKÜ, KF, sample 1 | 7.5 | 40.7 | 81.6% |
| 250/183, ZKÜ, KF, sample 2 | 8.2 | 38.6 | 78.8% |
| 250/183, ZKÜ, KF, sample 3 | 8.5 | 40.2 | 79.9% |
| IR medium value of the 3 samples |  |  | 79.7% |

Figure 2A:
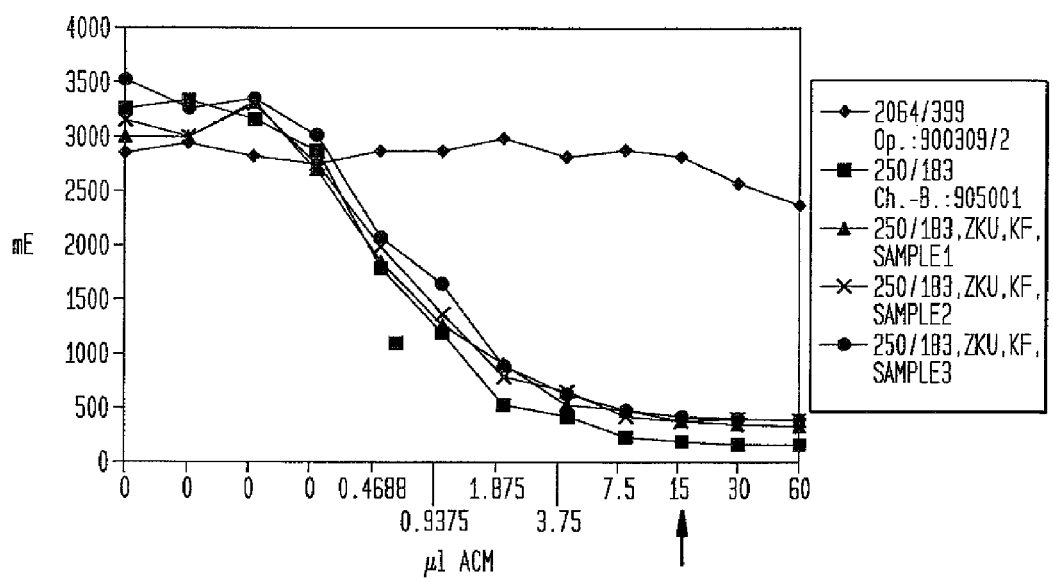
FIGS. 2A-E are graphs of results of a modified Lindmo test for the antibody preparations.

The results are shown in the graph of FIG. 2A.
b) Purified Mab-End Product (Mab) according to Conventional Fermentation (KF) and Conventional Purification (KR)

TABLE 2

|  | Tested mass in ng | Starting mass in ng | Immuno reactivity |
|---|---|---|---|
| negative control | — | 50.0 | — |
| positive control | 3.2 | 48.0 | 93.3% |
| 250/183, Mab, KF + KR, sample 1 | 7.3 | 24.8 | 70.6% |
| 250/183, Mab, KF + KR, sample 2 | 8.1 | 28.8 | 71.9% |
| 250/183, Mab, KF + KR, sample 3 | 8.4 | 32.4 | 74.1% |
| IR medium value of the 3 samples |  |  | 72.2% |

Figure 2B:
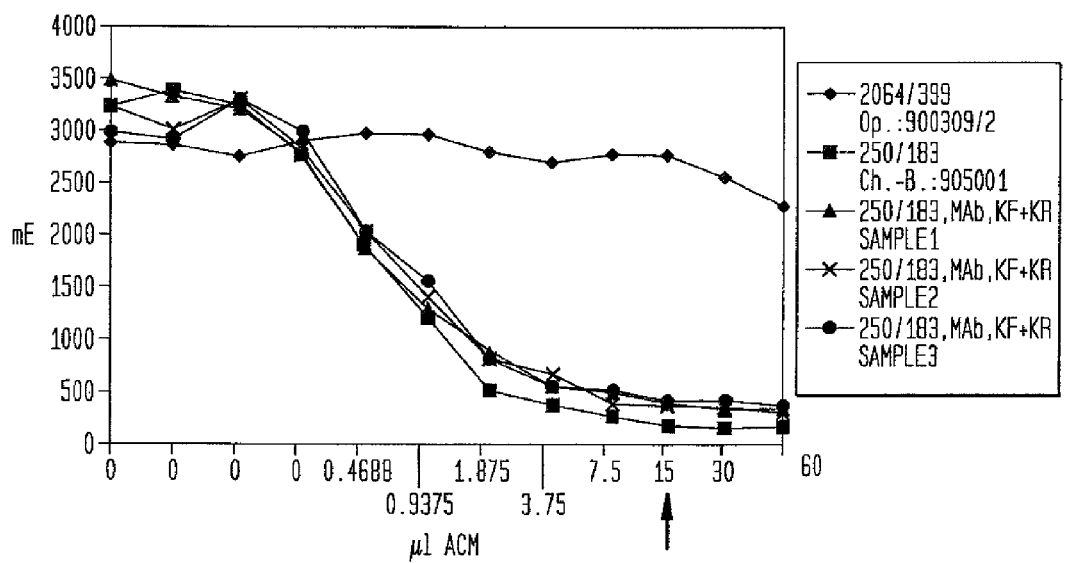

The results are shown in the graph of FIG. 2B

2. Fermentation in the Fluidized Reactor and Conventional Purification Method or "Column Reduced" Purification Method (Invention).
a) Cell Culture Supernatant (ZKÜ) after Fluidized Fermentation (WF)

TABLE 3

|  | Tested mass in ng | Starting mass in ng | Immuno reactivity |
|---|---|---|---|
| Negative control | — | 50.0 | — |
| positive control | 3.5 | 45.2 | 92.4% |
| 250/183, ZKÜ, WF, sample 1 | 3.7 | 183.5 | 98.0% |
| 250/183, ZKÜ, WF, sample 2 | 4.0 | 137.8 | 97.1% |
| 250/183, ZKÜ, WF, sample 3 | 3.9 | 123.0 | 96.8% |
| IR medium value of the 3 samples |  |  | 97.3% |

Figure 2C:
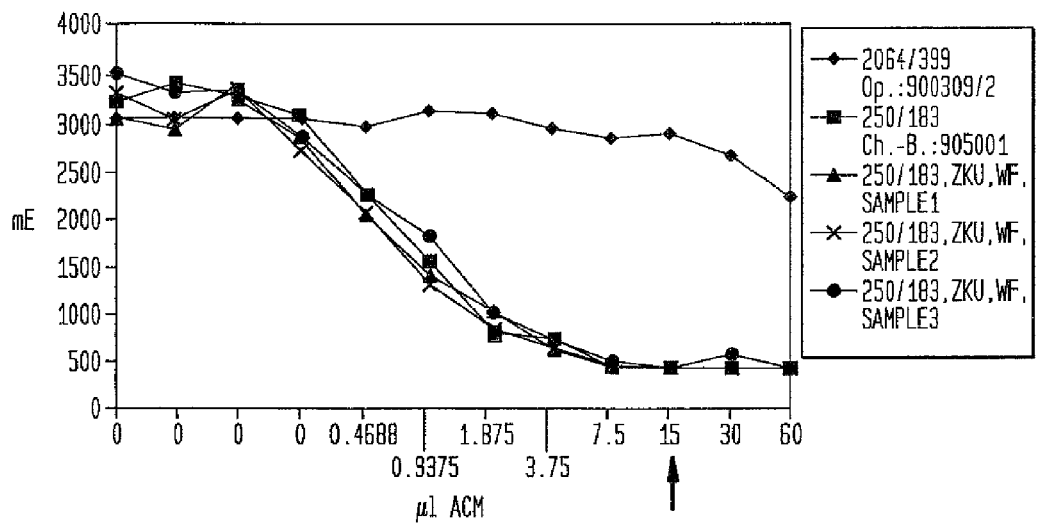

The results are shown in the graph of FIG. 2C.
b) Purified Mab-End Product (Mab) according to Fluidized Bed-Fermentation (WF) and Conventional Purification (KR)

TABLE 4

|  | Tested mass in ng | Starting mass in ng | Immuno reactivity |
|---|---|---|---|
| negative control | — | 50.0 | — |
| positive control | 3.5 | 45.2 | 92.4% |
| 250/183, Mab, WF + KR, sample 1 | 3.6 | 39.5 | 90.9% |
| 250/183, Mab, WF + KR, sample 2 | 4.1 | 35.6 | 88.5% |
| 250/183, Mab, W + KR, sample 3 | 3.9 | 34.6 | 88.7% |
| IR medium value of the 3 samples |  |  | 89.3% |

Figure 2D:
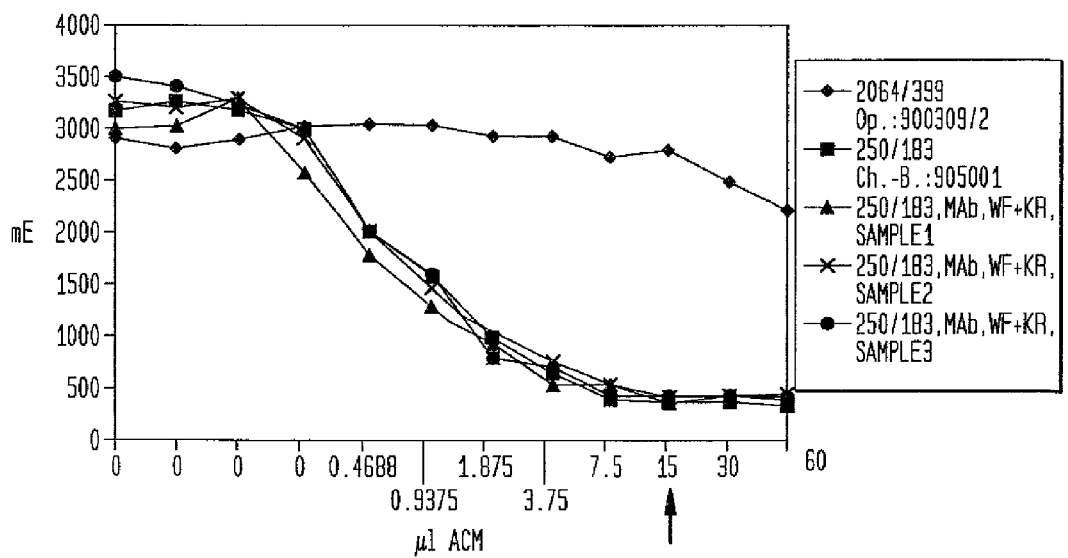

The results are shown in the graph of FIG. 2D.
c) Purified Mab End-Product (Mab) after the Fluidized Bed Fermentation (WF) and "Column-Reduced" Purification (SR)

TABLE 5

|  | Tested mass in ng | Starting mass in ng | Immuno reactivity |
|---|---|---|---|
| negative control | — | 50.0 | — |
| positive control | 3.5 | 45.2 | 92.4% |
| 250/183, Mab, WF + SR, sample 1 | 3.5 | 81.4 | 95.7% |
| 250/183, Mab, WF + SR, sample 2 | 3.9 | 99.5 | 96.1% |
| 250/183, Mab, W + SR, sample 3 | 4.0 | 100.5 | 96.0% |
| IR medium value of the 3 samples |  |  | 95.9% |

Figure 2E:
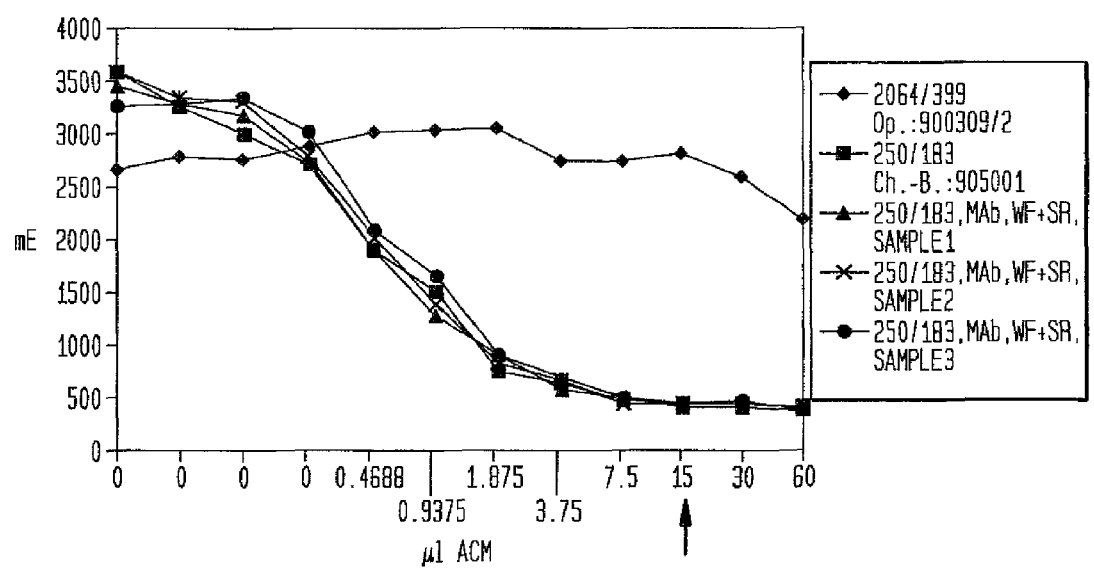

The results are shown in the graph of FIG. 2E.

The end results of Example 1 are summarized in the following Table 6.

Immunoreactivity of Mab BW 250/183

|  | conventional fermentation procedure and conventional purification method | Production Procedure 1 Fluidized reactor-fermentation and conventional purification method | Production Procedure 2 Fluidized reactor-fermentation and "column reduced" Purification method |
|---|---|---|---|
| Cell culture supernatant | 80% | 97% | 97% |
| Purified Mab final product | 72% | 89% | 96% |

The immunoreactivity of Mab BW 250/183 is distinctly dependent on the fermentation and purification conditions. With conventional fermentation, typically immunoreactivity in the cell culture supernatant up to 80% can be reached. However with the new fermentation method via the fluidized reactor, the immunoreactivity at 97%- is distinctly higher.

Likewise, the purification method affects the immunoreactivity of Mab. The novel "column-reduced" purification method is distinctly more gentle than the conventional purification method. (8% drop of immunoreactivity with the conventional method as compared to only a 1% drop with the new "column-reduced" purification method).

Comparable results were realized also with other Mabs for example with Mab BW 431/26 (Eur. J. Nucl. Med. 14 (1988), 523-528 and Int. J. Cancer 36 (1985), 75-84), Mab BW 575/931 (Pediatr. Hematol. Oncol. 6 (1989), 73-83), Mab YTH 24.5 (J. Immunol. 134 (1985), 3056-3061 and Leucocyte Typing III: White Cell Differentiation Antigens (publ. McMichael et al.), Oxford University Press, Oxford, pp 788-803), Mab BW 278/105 (J. Histochem. Cytochem. 34 (1986), 209-214), the Mab as described in the German patent application 197 44 531.4 as well as the fusion proteins described in British J. Cancer 645, 234-238, 1992. (see table 7).

TABLE 7

Immuno Reactivity In Dependence of Fermentation and Purification Method

| Name of Mab | conventional fermentation procedure and conventional purification procedure | Production Method 1 Fluidized reactor-fermentation and conventional purification method | Production Method 2 Fluidized reactor-fermentation and "column reduced" Purification method |
|---|---|---|---|
| BW 431/26, ZKÜ* | 85% | 96% | 96% |
| BW 431/26, GME* | 79% | 87% | 94% |
| BW 575/931, ZKÜ* | 75% | 93% | 93% |
| BW 575/931, GME* | 67% | 85% | 91% |
| YTH 24.5, ZKÜö | 83% | 98% | 98% |
| YTH 24.5, GMEö | 77% | 89% | 96% |
| BW 278/105, ZKÜ* | 87% | 94% | 94% |
| BW 278/105, GME* | 81% | 85% | 92% |
| Fusion Protein ZKU* | 84% | 97% | 97% |
| Fusion Protein GME* | 76% | 88% | 96% |

ZKÜ = Cell culture supernatant
GME: purified Mab-product

Since comparable findings were realized with all tested Mabs and a very complex (glyco-) protein, the fusion protein (molecular weight of the tetramer under native conditions 500 kDA), it can be assumed that comparable values will be realized with all Mabs and (glyco-) proteins that can be fermented in procaryotic and eucaryotic systems and that on that basis, a generalization of the positive results justified.

The Mab charges produced by conventional methods and purified according to method I and II showed an immunoreactivity after radio-labeling according to the method as described by Schwarz and Steinstrasser (J. Nucl. Med. 28 (1987), 721) an immunoreactivity, which was identical to that of the purified Mab protein in within the scope of the precision as in the Lindmo-test. The data are summarized in the following Table 8:

TABLE 8

| purified Mab-final product | conventional fermentation procedure and conventional purification method | Production Method 1 Fluidized reactor-fermentation and conventional purification method | Production Method 2 Fluidized reactor-fermentation and "column reduced" purification method |
|---|---|---|---|
| unmarked | 72% | 89% | 96% |
| Tc-99m marked | 70% | 89% | 95% |

Unexpected Clinical Results

Aliquots of preparations of the Mab BW 250/183, which were produced either by following conventional production methods (i. e. batch fermentation in stirred fermenters followed by conventional protein chemical purification; immunoreactivity 72%) or, the novel production method II (fluidized reactor followed by "column-reduced" purification method; immunoreactivity 96%) according to GMP were labeled with Tc-99m according to the method of Schwarz and Steinstraesser (J. Nucl. Med., 28 (1987), 721). The portion of the isotope bound to the Mab was in both preparations 99.9%. Patients that were believed to have inflammatory diseases respectively bone marrow metastasized tumors were given a dose of 10-20 m Ci i.v. (intravenously) of the radio-chemical identical Mab-preparation. Full body Scintigrams from dorsal view and frontal view were taken in the time intervals of from 2 to 25 hours after i.v. application of the radio-labeled Mab.

Surprisingly, it was found from the Scintigrams that after injection with Mab charges that had an immunoreactivity of <90% (production method II) that preferentially the bone marrow was sharply contoured and the spleen was more or less distinctly shown (see Example 3: images GRAN 91, GRAN 81 and GRAN 71). With Mab charges which are produced according to a conventional fermentation and purification method (immunoreactivity 70 to 80%) apart from the bone marrow image, the liver and the spleen were distinctly seen (see Example 3: images GRAN 11 and GRAN 21). Furthermore, theses images show a higher background, which is seen in the Scintigram as slightly foggy and out of focus.

As a result, the epitope-negative normal tissue of patients, who received Mab charges with an immunoreactivity >90% were burdened substantially less than those patients, who were treated with Mab charges with an immunoreactivity <80%. These observations on patients demonstrate the significance of the level in immunoreactivity of a specific Mab against granulocytes for the images (scintigraphy) in nuclear medicine. The Mab charges with an immunoreactivity >90% show distinct advantages not only in the imaging but also for the therapy with α- and β-emittors. Thus, it is for example possible that after labeling of the Mab charges with an immunoreactivity of ≥90% to couple $Re^{188/186}$, $Y^{90}$ or astatine by methods known from the literature to thus carry out a preferential bone marrow irradiation (Visser et al., J. Nucl. Med. 34 (1993), 1953-1963; Griffith et al., Cancer res. 51 (1991), 4594-4602; Denora et al., Anticancer Res. 17 (1997), 1735-1744).

Within the frame work of a treatment assay, a collective of 19 patients with acute myeloic leukemia or chronic myeloic leukemia were treated. For that purpose charges of the Mab BW 250/183 (immunoreactivity >90%) labeled with Re[188] (specific activity; 5-7.5 GBq/mg) and 6.5-12.4 GBq were applied (i.v.) intravenously.

Dosiometric research resulted in the data as collected in the following table.

treating with preparations with about 80% immunoreactivity because of over irradiation by lung and liver activity concentration.

In summary it can be said that the surprising advantages relative to the image quality, diagnostic efficiency, dosiometry and therapeutic efficiency which are generated due the use of high immunoreactive charges of Mab BW 250/183 in connection with $\alpha$-, $\beta$- or $\gamma$-emitters were not to be expected either qualitatively or quantitatively but will open the road to a more efficient diagnostic tool of inflammatory processes and of metastases as well as therapies for leukemia and other diseases of the hematopoietic system.

TABLE 9

Dosiometric Research after Radio Immunotherapy with Re-188-labeld Mab BW 250/183

| Sex | Age | Disease | Marker | Date of KM-Transplantation | Organ Dosis in Gy | | | | |
|---|---|---|---|---|---|---|---|---|---|
| | | | | | KM | Mz | Lb | Nie | Lu* |
| f | 39 | AML | T (8; 21) | February 1998 | 12.0 | 7.3 | 3.8 | 5.3 | n.d. |
| f | 38 | AML | no | March 1998 | 13.0 | 13.2 | 6.2 | 11.3 | n.d. |
| m | 52 | AML | no | March 1998 | 8.0 | 7.0 | 5.0 | 11.0 | n.d. |
| m | 45 | AML | no | April 1998 | 13.0 | 12.0 | 4.0 | 11.0 | n.d. |
| m | 50 | CML | T (12; 13) | April 1998 | 12.8 | 18.6 | n.d. | 7.6 | n.d. |
| f | 19 | c-ALL | no | May 1998 | 5.9 | 12.3 | 1.8 | 7.1 | n.d. |
| m | 44 | c-ALL | Ph+ | June 1998 | 15.2 | 12.7 | 3.2 | 5.3 | 0.3 |
| f | 17 | AML | no | July 1998 | 18.4 | 10.3 | 4.1 | 5.0 | n.d. |
| m | 50 | AML | T (15; 17) | August 1998 | 10.9 | 8.6 | 2.7 | 4.4 | 0.4 |
| f | 32 | AML | Deletion Chrom. 6 | September 1998 | 15.7 | 6.8 | 3.0 | 5.1 | 0.9 |
| m | 56 | B-CLL | no | September 1998 | 15.7 | 4.0 | 2.3 | 4.5 | n.d. |
| f | 36 | AML | no | September 1998 | 13.0 | 5.6 | 2.3 | 15.1 | 0.6 |
| m | 45 | c-ALL | Ph+ | November 1998 | 6.5 | 11.5 | 2.7 | 4.5 | n.d. |
| f | 19 | AML | T (9; 11) | November 1998 | 11.4 | n.d. | 7.2 | 10.1 | 1.1 |
| f | 40 | 2. AML (MDS) | no | December 1998 | 13.8 | 18.2 | 5.3 | 10.1 | 0.3 |
| m | 51 | AML | Trisomie 6, 8, 21 Deletion 11q23 | December 1998 | 14.3 | 6.7 | 5.9 | 8.9 | 0.4 |
| m | 20 | CML | Ph+ | December 1998 | 11.9 | 14.3 | 7.0 | 5.5 | n.d. |
| f | 47 | 2. AML Plasmocytoma, MDS | T (16; 19) P (11; 12) | December 1998 | 16.2 | 7.6 | 3.7 | 5.6 | 0.5 |
| m* | 59 | AML | no | December 1998 | 19.0 | 14.0 | 6.0 | 8.2 | 0.7 |

*KM = bone marrow; Mz = spleen; Lb = liver; Nie = kidney, Lu = lung

The data show, that it is possible to localize high radiation doses on the bone marrow and the spleen of a patient with leukemia by means of radio immunotherapy with the Re-188 labeled Mab BW 250/183 (immunoreactivity >90%)

The patient group consisted of persons with a relapse risk of 40-50% within 2 years. Surprisingly, the radio immunotherapy induced no significant side effects. After that, a standard therapy followed consisting of 12 Gray full body irradiation sessions and dispensation of cyclophospho amide. All 19 patients could be brought into complete remission, pointing to a future role of radio immunotherapy with Mab BW 250/183 for treating leukemia in conjunction with the standard therapies. It also appears possible that radio immunotherapy will replace the full body irradiation with its negative side effects.

A further advantage in using Mab B W 250/183 with an immunoreactivity of >90% percent is that the administered amount of 1 mg per application can be reduced to 0.5 mg per application. This reduction leads to an HAMA (human-anti-mouse-antibody)-frequency which was under 2% and which therefore did not deviate significantly from the background HAMA values of normal persons.

Furthermore, it is surprising that early metastases in RES (reticulo-endothelial systems) of the bone marrow could be discovered with Mab preparations, which had an immunoreactivity of ≥90% that could not definitely be detected when

EXAMPLE 2

Production Method 1

Culturing Eukaryotic Cells and their Fermentation in a Fluidized Reactor

An ampoule from the working cell bank, stored in liquid nitrogen is being defrosted and the cells contained therein are cultivated under standard cell culture conditions (synthetic protein-free cell culture medium) in T-flasks. When a cell titer of 6-10×10[7] has been reached, the content of 4-6 T-flasks is further cultivated in a 500 ml-Spinner container under standard cell culture conditions. After reaching cell titer of 1.5-2×10[8], the cells are then transferred into 2 Spinner containers each of 1000 ml volume and cultivated further. After reaching a cell titer of 1.2-1.5×10[9], the cells are inoculated in a 900 ml cell culture medium and 200 ml Siran$^{R-}$ carrier containing fluidized reactor (Bioreactor Pilot B 500, Papaspyrou Biotechnologie GmbH, Technologiezentrum Jülich, D-52428 Jülich) and cultivated in accordance with the directions of the Papaspyrou Biotechnologie company for 60 days at 36.5° C. Oxygen content, pH value, glucose concentration and the Mab-content are being controlled in intervals of 1-4 days. During fermentation the cell culture supernatant is continuously harvested and stored at 4° C.

Proteinchemical Purification with the Conventional Method

The volume of the cultured ultraconcentrate to be processed is determined and then 1.5 times the amount of saturated ammonium sulfate slowly added. The suspension remains at 4° C. for up to three days until a clear supernatant is seen. This supernatant is being decanted and the precipitate suspended in the remaining amount of the supernatant and spun off at >5000 g for 30 minutes at room temperature. Sediments are combined in a centrifuge beaker (⇒ Mab ammonium sulfate paste) and subsequently dissolved with a starting buffer (1 to 4 parts buffer to one part sediment).

The amount of dissolved sediment which is computed for a protein A run is combined under stirring with a watery Triton X-100 solution, 100 g/l so that the end concentration of Triton X-100 is 0.5 percent (50 ml Triton X-100 solution per 1000 ml sediment in solution). The formulation is subjected to sterile filtration through a spray filter, 0.2 µm. The formulation then remains at rest for 2-18 hours at 4° C. (⇒ virus inactive Mab solution).

Immediately thereafter, the protein A fractionation is carried out. The application of the sample is carried out under possibly aseptic conditions and by means of a pump, wherein the flow speed can correspond to a 1-2 fold volume per hour, so that there is contact between Mab and Protein A for at least 30 minutes. After the solutions have been completely applied, the proteins not binding to Protein A and Triton were being washed from the column with starting buffer and are rinsed until the extinction/transmission of the flow-off indicates the beginning value of the starting buffer again (duration: 0.5 to 3 hours). The elution of the Mab is carried out with elution buffer of pH 3.0. The eluate collected in a container cooled with ice flakes (weighed glass bottle) and containing about 0.1 of the column volume of 2 M Tris/HCl, pH 8.0. The elution is carried until the writer indicates that the starting value has been approximately reached again. (⇒ purified Mab solution).

After determining the volume, a 1.5 fold amount of saturated ammonium sulfate-solution is added slowly under stirring for 60 minutes. Thereafter the suspension remains standing for up to 3 days at 4° C. until a clear supernatant has formed. The batch is shaken and spun at >5000 g for 30 minutes at room temperature. The supernatant is then decanted and the sediments are combined in a centrifuge beaker. (⇒ Mab-ammoniumsulfate paste) and dissolved most concentrated in tris/HCl-NaCl-buffer (1-3 parts of buffer to 1 part of sediment).

The cleared protein solution is immediately applied to a regenerated Sephadex G-25 column equilibrated with Tris/HCl-NaCl-buffer, pH 7.5. The protein solution volume that is to be salt-converted should at the most be 15% of the column volume. The solution coming from the column is fed through a flow-through photometer and subsequently led through a pH-/Ionmonitor. After the Mab solution is completely applied, the column is rinsed with Tris/HCl-NaCl-buffer, pH 7.5 at a flow speed in the column of about 20 ml per cm$^2$ per hour. The Mab which runs in the exclusion volume of the column is collected in a sterile receptacle until the line UV writer again indicates the starting value of the extinction/transmission (about 95%). The pH-/Ion monitor is not yet supposed to show a change in conductivity (⇒ rebuffered Mab-solution).

The conductivity of the solution is checked and if necessary adjusted to the conductivity of the buffer for injection purposes by adding sodium chloride solution, 10 g/l of water.

The product is then applied to a prepared Q-Sepharose-column possibly under aseptic conditions and with an application speed of 150 ml per hour (per ml Q-Sepharose 2 to 5 mg protein). The elution is carried out with Tris/HCl-NaCl-buffer, pH 7.5 with a flow speed of about 25 ml per cm$^2$ and per hour. The solution coming from the column is fed over a flow-through photometer and subsequently led over a pH-Ion monitor. The Mab flowing from the column is collected in a sterile receptacle according to the UV line writer profile until the line writer indicates approximately the extinction/transmission starting value (about 95%) (⇒ de-pyrogenated Mab-solution).

The pH value of the Mab-containing eluate is adjusted after the anion exchange chromatography with 1N HCl or 1N sodiumhydroxide solution to a pH of 6.9.

After determining the volume, 1.5 times the amount of saturated ammoniumsulfate-solution is again added slowly under agitation and stirred for 60 minutes at 4° C. Thereafter, the suspension remains standing overnight until a clear supernatant has formed. This formulation is shaken and spun at 8525 g in a centrifuge at room temperature for 60 minutes. Then the supernatant is decanted and the sediments combined in a centrifuge beaker (⇒ Mab-ammoniumsulfate paste) and dissolved in most concentrated form in sodiumphosphate-NaCl-sorbit-buffer, pH 7.2 (1 to 3 parts buffer to 1 part sediment).

The cleared protein solution is immediately applied under possibly aseptic conditions (at most 15% of the column volume) to a regenerated G-25 Sephadex column which has been equilibrated with sodiumphosphate-NaCl-sorbit buffer, pH 7.2. The solution coming from the column is led over a flow-through photometer and subsequently over a pH-/ion monitor. The column is then rinsed with sodium phosphate-NaCl-sorbit buffer, pH 7.2 (flow speed about 20 ml per cm$^2$ and per hour). The Mab which comes from the exclusion volume of the column is collected in a sterile container according to the UV-line writer profile until the line writer indicates again approximately the extinction/transmission starting value (about 95%). The pH-/ion monitor should not yet indicate a change in the conductivity (⇒ Mab-bulk solution, concentrated)

The pH value of the solution is checked and adjusted to pH 7.2 with 1N HCl or 1 N sodiumhydroxide solution.

By means of the values for the mouse IgG-concentration and the volume, the "final bulk" is diluted with sodiumphosphate-NaCl sorbit-buffer, pH 7.2 to the desired final concentration.

The product is then sterile-filtrated over a 0.2 µm-one-time filter and divided into aliquots and stored as the "final bulk" at −20° C.

Production Method II

Culturing of Eukaryotic Cells and their Fermentation in a Fluidized Reactor

An ampoule from a working cell bank stored in liquid nitrogen is defrosted and the cells contained therein cultivated according to standard cell culture conditions (synthetic protein-free cell culture medium) in T-flasks. After the entire cell count has reached 6-10×10$^7$, the content of 4-6 T-flasks is further cultivated in a 500 ml Spinner container under standard cell culture conditions. After the cell count reaches 1.5-2×10$^8$, the cells are transferred to 2 Spinner containers each with 1000 ml volume and further cultivated. After reaching a cell count of 1.2-1.5×10$^9$, the cells are inoculated in a fluidized reactor (Bioreactor Pilot B 500, Papaspyrou Biotechnologie GmbH, Technologiezentrum Jülich, D-52428 Jülich)

containing 900 ml cell culture medium and 250 ml Siran$^R$ carrier and cultivated in accordance with the methodology of the Papaspyrou Biotechnologie GmbH for 60 days at 36.5° C. Oxygen content, pH value, glucose concentration and Mab-content are checked in intervals of 1 to 4 days. During the fermentation, the cell culture supernatant is continually harvested and stored at 4° C.

Protein-Chemical Purification with a "Column-Reduced" Method.

After harvesting 18 l cell culture medium, a cell separation follows by means of "tangential flow" micro filtration followed by a sterile filtration through a 0.2 μm filter. The cell-free and sterile cell culture harvest is stored at 20° C. until sufficient cell culture harvest was collected for a subsequent purification (cell culture harvest of about 250 l cell culture medium). After the desired batch size has been reached, the sterile cell culture harvest is defrosted, cleared through microfiltration and concentrated 100 to 150 times by means of ultra filtration. Thereafter, the ultra concentrate is combined with the same volume of 2 times concentrated° starting buffer (pH8.6) and sterile filtrated. A sterile Triton X-100 solution (100 g Triton/l) ad 0.5% Triton end concentration is added under stirring. The solution is left standing for 4 to 18 hours at 4° C. in order to inactivate the coat-containing viruses.

Thereafter, the ultraconcentrate treated with Triton is pumped onto a Protein A-Sepharose-4-fastflow column, which was equilibrated previously with 5 times the column volume of starting buffer. Proteins that are non-binding and Triton X100 are washed from the column with 5 column volumes starting buffer. Subsequently, Mab linked to the A-protein is washed from the column with the elution buffer (pH 3.0) and collected in 130 ml neutralization buffer (pH 8).Thereafter, the Mab which has been collected in neutralization buffer is adjusted to a pH of 7-7.5 with NaOH depending on need, then diluted with the same volume of 2× membrane adsorbing buffer (pH 7.5) and sterile filtrated. Subsequently, the Mab solution is pumped under sterile conditions through a membrane adsorber, which was previously equilibrated with WFI and the adsorption buffer (pH7.5). The flow-through containing the Mab now free from contaminating pyrogens and DNA is collected in a sterile container and adjusted with buffer (pH 7.5) to 500 μg Mab/ml. Thereafter the diluted Mab solution undergoes ultrafiltration with a Viragard-hollow fiber module to remove potentially contaminating viruses. The permeate which contains the virus-free Mab is concentrated by means of ultrafiltration to a concentration of 4-5 mg Mab/ml and diafiltrated against an endbuffer (pH 7.2). After sterile-filtration, dilution by end buffer and renewed sterile-filtration the Mab is stored as bulk material.

EXAMPLE 3

Modified Quantitative Immunoreactivity Test according to Lindmo

Introduction:

In order to determine the content of immunoreactive monoclonal antibodies in hybridoma supernatants, a binding assay with an excess amount of antigen in combination with a sensitive (1-2 ng mouse-Ig/ml) ELISA-system was used for the determination of the portion of unbound monoclonal antibodies. This test has essentially two advantages as compared with the immunoreactivity test developed by Lindmo, namely a) the test permits determining the immunoreactivity of un-purified as well as purified non-radio labeled and radio labeled Mab; and b) the test permits determining the immunoreactivity in the absence of unspecific binding.

Material 1.1 Chemicals and Materials

| Name | Manufacturer | Order No. |
|---|---|---|
| Formaldehyde solution, 37% | Merck | 818708 |
| Sodium dihydrogen-phosphate-1-hydrate | Merck | 6346 |
| Di-sodiumhydrogen-phosphate-2-hydrate | Merck | 30412 |
| PBS | Behringwerke | |
| Glycin | Merck | 104201 |
| 96 well micro titer plates, Type B | Nunc | 4-60445 |
| Goat-anti-mouse-IgG ("catcher") | Sigma | M8642 |
| Tween PBS for Enzygnost | Behringwerke | OSWE96 |
| Casein | Sigma | C5890 |
| Goat-anti-mouse IgG,-antibody coupled with alkaline phosphates | SBS | 107-04 |
| 4-methyl-urnbelliferyl-phosphat | Sigma | M 8276 |
| SDS | Sigma | L 5750 |

1.2 Instruments

| | | |
|---|---|---|
| Centrifuge | Heraeus | |
| Minitubes, 1.0 ml | Kühn & Bayer | 64698446 |
| Rotation instrument | Heidolph | Reo x2 |
| Analytical scale Mettler | DE 100 | |
| Magnetic stirrer IKA | RCT | |
| pH-meter | WTW | |
| Moulinette | moulinex | |
| Fluoroskan | Merlin | |

Preparation of Solutions Needed

4% formaldehyde solution according to Lilly
  to 100 ml 37% formaldehyde solution,
  900 ml aqua bi-distilled is added. In this solution
  4 g sodium hydrogen diphosphate and
  6.5 g di-sodium hydrogen phosphate are dissolved under stirring.
  The pH value of this solution is pH 7.0

Rinsing Solution: 0.05 Tris-Citrate-Buffer pH 7.4
  6.06 gTris
  19.5 g citric acid-1-hydrate and
  4.25 sodium hydroxide
  are dissolved ad 1 l aqua bi-distill.

Blocking Solution: 1% Casein in PBS, pH 7.2
  10 g casein in
  1 l cold PBS, pH 7.2+phenol red
  stir 30 minutes
  thereafter spin at 3000 rpm and
  filter supernatant through a folding filter.
  pH-value of the solution is adjusted with NaOH Substrate Buffer: 0.5 Tris, 0.01% MgCl, pH 9.6
  60.57 g Tris and
  0.1 g magnesiumchloride are dissolved
  add 1 l aqua bi-distill.

4-Methyl-Umbelliferyl-Phosphate (MUP) Solution
  concentration of the MUP solution is 1 mg 4-MUP/4 ml substrate buffer.

Stop-Solution: 0.2 M Glycine, 02. % SDS, pH 11.7
  15 g glycine and
  2 g SDS are dissolved in
  ad 1 l aqua bi-distill.
  The pH value of the solution is adjusted with 5N NaOH.

Modified Quantitative Immunoreactivity Test according to Lindmo

1. Production of the Antigen containing Materials ("Antigen containing Material", ACM)

Tissue of human Tumor-Xenografts (MZ-STO 1, stomach carcinoma), which express the epitope of the BW 250/183 (at the membrane of granulocytes expressed "non-specific cross reacting antigen" (NCA-95)) are being cut up in a Moulinette into 2 to 5 mm pieces and fixed according to Lilly in 4% formaldehyde solution for at least 16 hours at room temperature.

After rinsing, the fixed tissues are passed through a stainless steel strainer.

The fixed cells are washed at least 10 times with PBS until the supernatant is approximately clear and then washed once with formalin solution.

This preparation is stored at 4° C. in formalin solution according to Lilly (1 Part ACM and 1 part formalin according to Lilly) and designated as "ACM".

2. Binding-Assay with Antigen Excess

The ACM is washed at least 10 times with PBS and subsequently, the pellet is suspended and incubated in a 100 mM glycine (4-times the pellet volume) for 30 minutes at 4° C.

Thereafter, the cells are again washed 4 times with PBS.

Increasing amounts of ACM are (0.1 up to 50 mg) are put in 1 ml minitubes and each minitube incubated with 500 µl hybridoma supernatant containing 25 ng Mab BW 250/183 overnight at room temperature (overhead-rotation).

Negative controls are incubated with 25 ng of the antimycoplasm Mab BW 227/7 having the same isotype (Ig ACM is spun off;

Supernatant is removed and the remaining mouse-IgG-molecules which are not bound to the ACM pellet are then analyzed.

3. Determination of the Portion of Unbound Mouse-IgG-Molecules in the ELISA-System Coating the Micro-Titer Plates with Antigen 96-well polystyrol-micro-titer plates are incubated at room temperature with 50 µl goat-anti-mouse-IgG-antiserum, 2.5 µl/ml, per well over night.

The rabbit-anti-mouse-IgG-antiserum is subsequently aspirated and the plates are washed 4 times with 0.5 M Tris-citrate buffer, pH 7.4 (1 washing round=200 µl washing solution per well pipetting and aspirating)

The micro-titer plates are dried overnight, inverted on cellulose.

The shelf life of the so pretreated micro-titerplates which are sealed in dry cartridges is at least 6 months.

Blocking of Free Binding Sites

200 µl blocking solution are pipetted per well and the plates are incubated at room temperature for 60 minutes.

Subsequently, the blocking solution is aspirated

Application of the Sample

50 µl of the ACM supernatants, to be analyzed for the number of unbound mouse-IgG-molecules, are applied per well and incubated at room temperature for 60 minutes.

Thereafter, the micro-titerplates are washed 3 times as afore-described with washing solution.

Amplification and Detection

50 µl of a goat-anti-mouse-IgG-antibody which has been coupled with alkaline phosphatase diluted at a ratio 1:250, is applied per well and incubated at room temperature for 30 minutes.

The micro-titer plates are washed 3 times with washing solution as afore-described.

50 µl MUP solution is applied per well and incubated at room temperature for 30 minutes.

The substrate reaction is stopped after the incubation at room temperature for 30 minutes by adding 100 µl stop solution.

Thereafter, fluorescence is measured: the start-up wavelength is 355 nm and the emission wavelength is 460 nm.

The test has a sensitivity in the range of 1 to 2 ng mouse IgG/ml.

Mathematical Determination of the Immunoreactivity

IR [%]=100%−[100%×(Mab-concentration in supernatant/Mab-starting concentration.)]

The computation of the immunoreactivity is carried out at the reading point. This point in the curve corresponds to that volume of ACM (X axis of the ELISA-curve) where a drop in the plateau value for the non-specific control (non-specific binding) has not yet shown up.

EXAMPLE 4

Scintigrams taken after Injection of Tc-99m Labeled Mab BW 250/185

The Mab charges utilized for the labeling with Tc-99m, vary in their immunoreactivity due to the type of production method. Data for these production methods are summarized in the following table 10

TABLE 10

Figure 3:
FIGS. 3 and 4 are scintigrams of monoclonal antibody labeled with TC-99m from prior art preparations.
Figure 4:
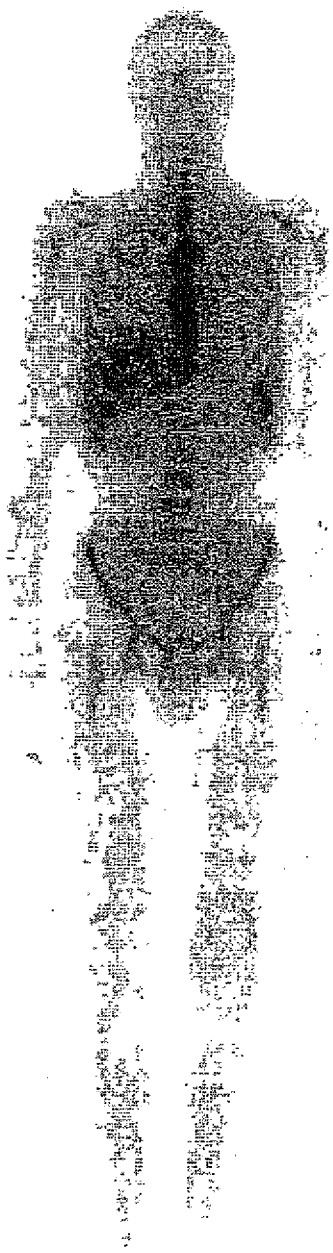
Figure 4:
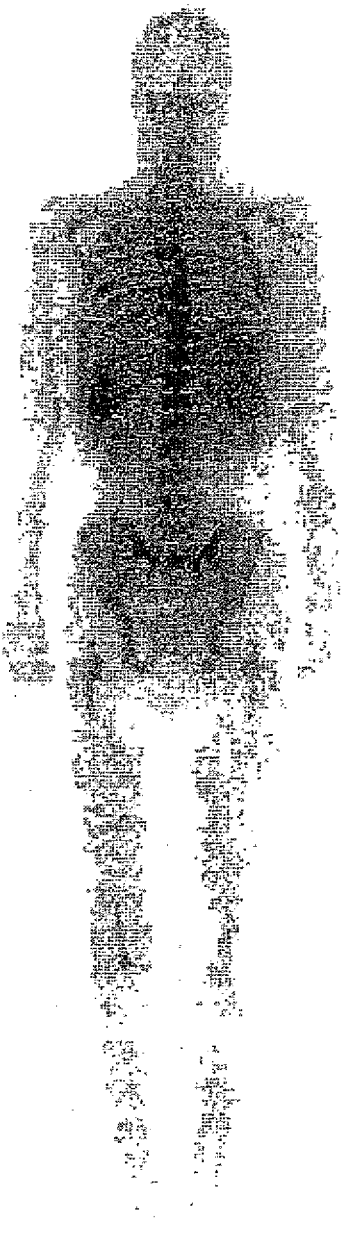
Figure 5:
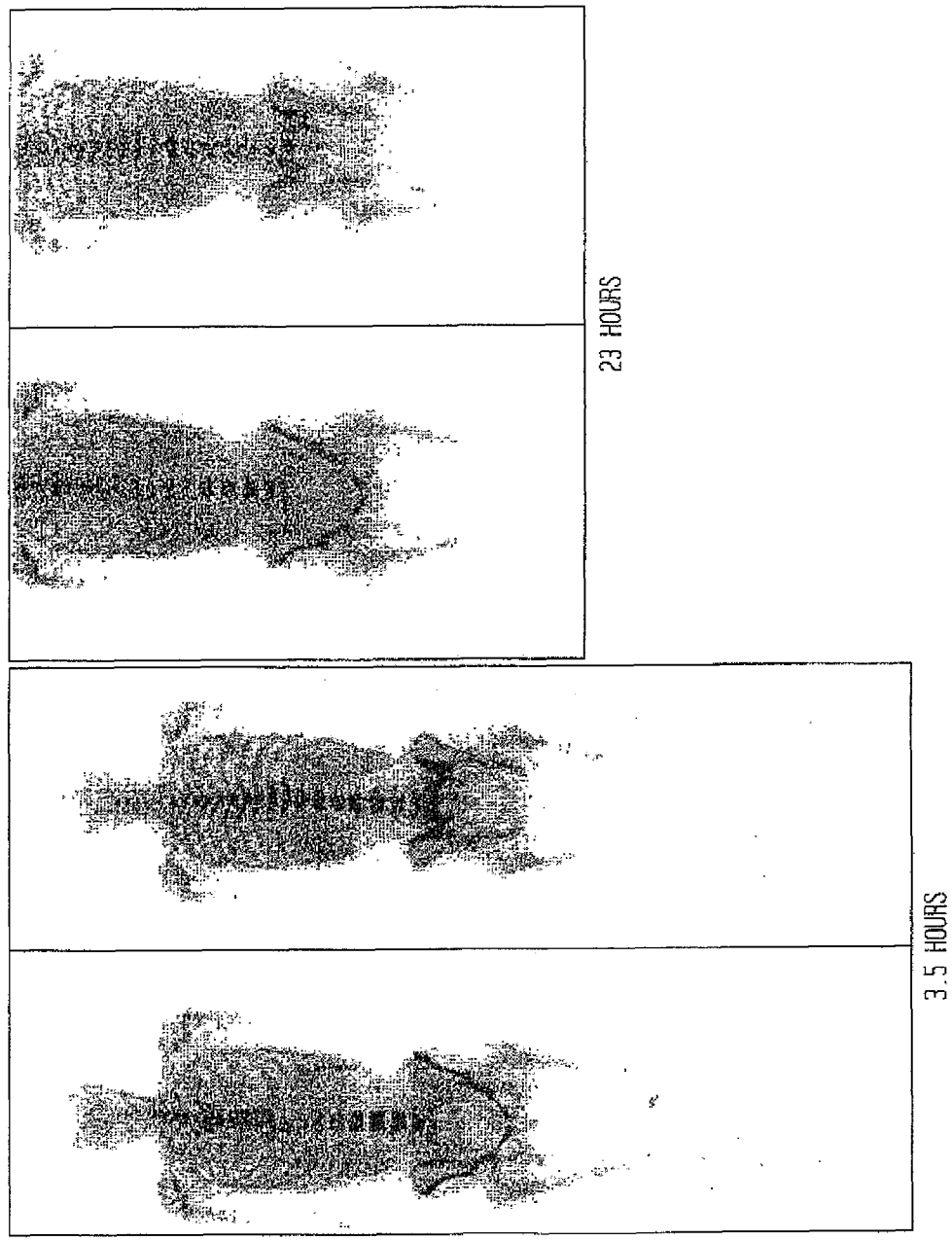
FIGS. 5 to 7 are scintigrams of TC-99m labeled monoclonal antibodies from preparations according to the present invention.
Figure 6:
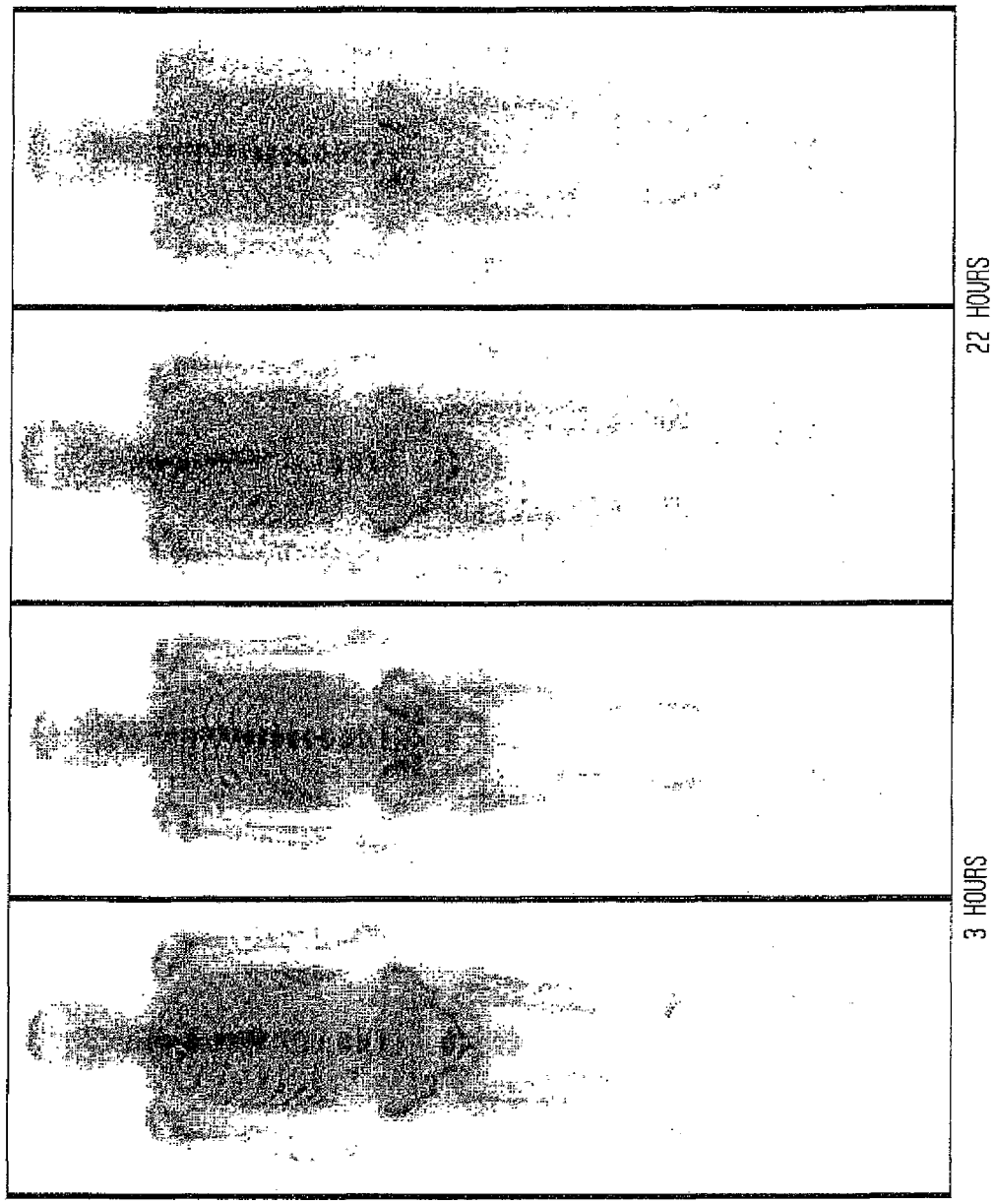
Figure 7:
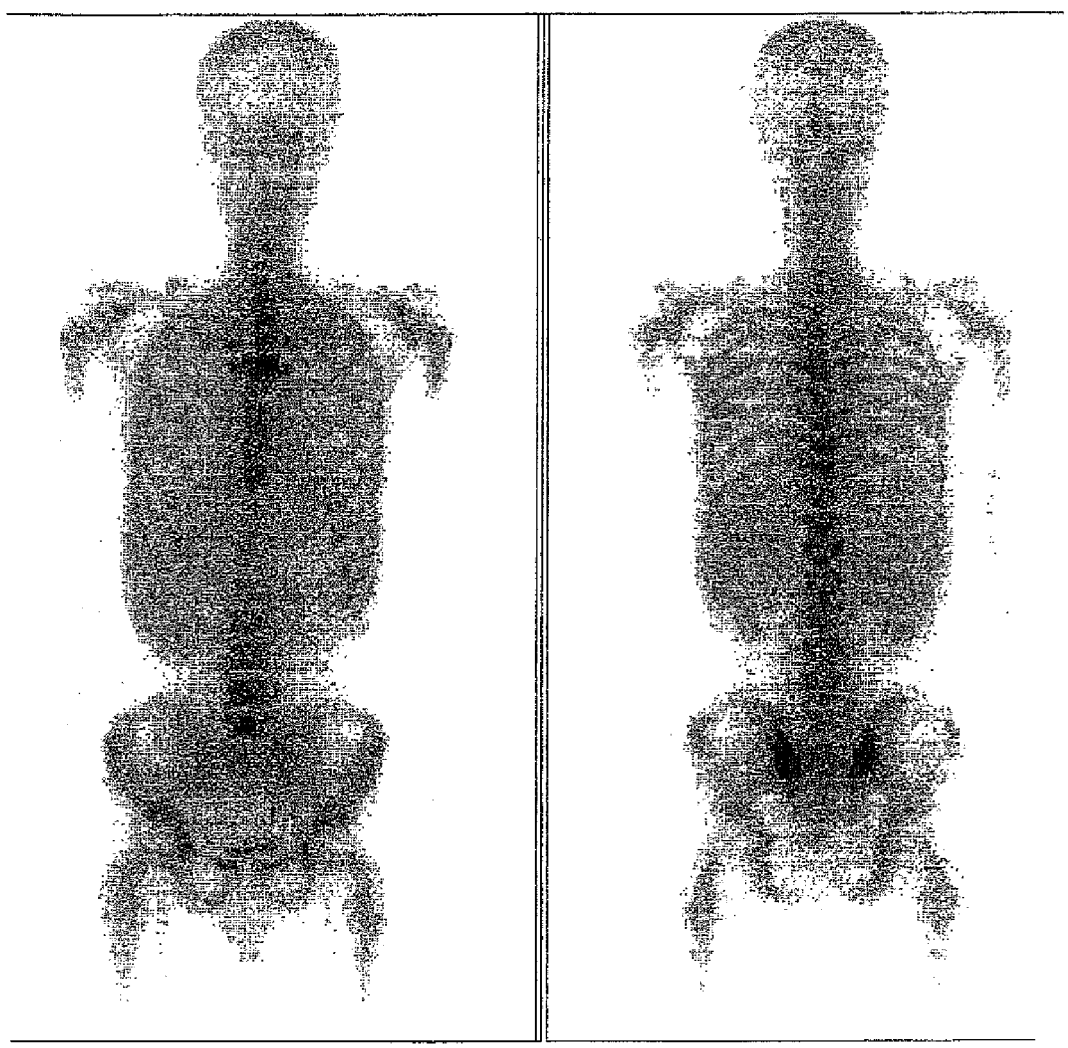

| Mab Charge | Production Method | Immunoreactivity | Scintigram |
|---|---|---|---|
| Mab BW 250/183 | Conventional fermentation method and conventional purification method | 70-80% | Image GRAN 11 (FIG. 3) Image GRAN 21 (FIG. 4) |
| Mab BW 250/183 | Fluidized reactor fermentation and "column reduced" method | >90% | Image GRAN 91 (FIG. 5) Image GRAN 81 (FIG. 6) Image GRAN 71 (FIG. 7) |

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A preparation of labeled immunoreactive antibody for therapeutic or diagnostic use, comprising:

an immunoreactive monoclonal, mouse chimeric or humanized antibody suitable for medical use that binds specifically to human CD66 a, b, c, e and having a greater than 90% antibody immune reactivity to human CD66 a, b, c, e, as determined by a modified Lindmo test, wherein the immunoreactive antibody is determined in a binding assay using excess amount of fixed cells comprising human CD66 antigen and the percentage of immunoreactive antibody that binds specifically to human CD66 a, b, c, e using the modified Lindmo test is calculated according to the formula:

Immunoreactive (IR) [%] =100%-[100%×(antibody-concentration in supernatant/antibody starting concentration)], and wherein the fixed cells have an epitope density of $>10^4$ per fixed cell, and wherein the immunoreactive antibody is a monoclonal antibody selected from the group consisting of BW 431/26 and BW250/183.

2. The preparation of claim 1, wherein the labeled immunoreactive antibody is coupled to a marker selected from the group consisting $^{99m}$Tc, $^{186}$Re, $^{188}$Re, $^{90}$Y and astatine.

3. The preparation of claim 1, wherein the immunoreactive antibody is produced by cells cultivated through fermentation of the culture medium in a fluidized reactor.

4. The preparation of claim 3, wherein the cells are recombinant eukaryotic host cells.

5. The preparation of claim 1, wherein the immunoreactive antibody is purified from a culture medium using a one-column protein A affinity chromatography.

6. The preparation of claim 4, wherein the eukaryotic host cells are hybridoma cells.

7. The preparation of claim 1, wherein the immunoreactive antibody thereof binds to the CD66 epitope on a cell membrane of at least one of malignant and non-malignant cells.

8. The preparation of claim 1, wherein the immunoreactive antibody binds specifically to an epitope at CD66e.

* * * * *